US011004558B2

(12) United States Patent
Sysko et al.

(10) Patent No.: US 11,004,558 B2
(45) Date of Patent: *May 11, 2021

(54) SYSTEMS AND METHODS FOR DISEASE CONTROL AND MANAGEMENT

(71) Applicant: Welldoc, Inc., Columbia, MD (US)

(72) Inventors: Ryan A. Sysko, Wilmington, DE (US); Suzanne K. Sysko, Wilmington, DE (US); James M. Minor, Newark, DE (US); Anand K. Iyer, Potomac, MD (US); Andrew V. Fletcher, Park City, UT (US)

(73) Assignee: Welldoc, Inc., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/074,194

(22) Filed: Oct. 19, 2020

(65) Prior Publication Data
US 2021/0035673 A1 Feb. 4, 2021

Related U.S. Application Data

(63) Continuation of application No. 16/186,996, filed on Nov. 12, 2018, now Pat. No. 10,818,389, which is a
(Continued)

(51) Int. Cl.
*G16H 20/60* (2018.01)
*G16H 50/50* (2018.01)
(Continued)

(52) U.S. Cl.
CPC ............ *G16H 20/60* (2018.01); *G16H 10/60* (2018.01); *G16H 20/17* (2018.01); *G16H 50/50* (2018.01); *G16H 70/20* (2018.01)

(58) Field of Classification Search
CPC .......... G16H 10/60; G16H 20/17; G06N 7/005
See application file for complete search history.

(56) References Cited

U.S. PATENT DOCUMENTS 3,810,102 A 5/1974 Parks, III et al.
4,173,971 A 11/1979 Karz
(Continued)

FOREIGN PATENT DOCUMENTS

WO WO 99/63462 12/1999

OTHER PUBLICATIONS

Montani et al., "Protocol-based Reasoning in Diabetic Patient Management," International Journal of Medical Informatics, Elsevier Scientific Publishers, Shannon, IR, vol. 53, No. 1, Jan. 1, 1999, pp. 61-77.
(Continued)

*Primary Examiner* — Reginald R Reyes
(74) *Attorney, Agent, or Firm* — Bookoff McAndrews, PLLC

(57) ABSTRACT

Methods, computer-readable media, and systems for providing disease management. In one implementation, a system develops a treatment recommendation for a patient based on patient data. The system may receive patient data, execute a basic model of the physiological system of the patient to generate a modified model for the patient based on the patient data, perform a statistical analysis of the patient data to detect data excursions of the parameter values; use the modified model to determine factors causing the data excursions; and use the model to develop a treatment recommendation to ameliorate negative effects of the disease.

19 Claims, 6 Drawing Sheets

Related U.S. Application Data continuation of application No. 15/670,551, filed on Aug. 7, 2017, now abandoned, which is a continuation of application No. 12/071,486, filed on Feb. 21, 2008, now Pat. No. 9,754,077.

(60) Provisional application No. 60/902,490, filed on Feb. 22, 2007.

(51) Int. Cl.
*G16H 70/20* (2018.01)
*G16H 10/60* (2018.01)
*G16H 20/17* (2018.01)

(56) References Cited

U.S. PATENT DOCUMENTS

| | | |
|---|---|---|
| 4,428,733 A | 1/1984 | Kumar-Misir |
| 4,439,242 A | 3/1984 | Hadden |
| 4,712,562 A | 12/1987 | Ohayon et al. |
| 4,731,726 A | 3/1988 | Allen, III |
| 4,803,625 A | 2/1989 | Fu et al. |
| 4,835,372 A | 5/1989 | Gombrich et al. |
| 4,838,275 A | 5/1989 | Lee |
| 4,960,118 A | 10/1990 | Pennock |
| 5,019,974 A | 5/1991 | Beckers |
| 5,036,462 A | 7/1991 | Kaufman et al. |
| 5,036,852 A | 8/1991 | Leishman |
| 5,077,476 A | 12/1991 | Rosenthal |
| 5,307,263 A | 4/1994 | Brown |
| 5,339,821 A | 9/1994 | Fujimoto |
| 5,346,008 A | 9/1994 | Bomn et al. |
| 5,377,258 A | 12/1994 | Bro |
| 5,390,238 A | 2/1995 | Kirk et al. |
| 5,437,278 A | 8/1995 | Wilk |
| 5,437,634 A * | 8/1995 | Amano ............... A61M 1/3643 604/65 |
| 5,465,082 A | 11/1995 | Chaco |
| 5,544,661 A | 8/1996 | Davis et al. |
| 5,569,212 A | 10/1996 | Brown |
| 5,596,994 A | 1/1997 | Bro |
| 5,601,435 A | 2/1997 | Quy |
| 5,626,144 A | 5/1997 | Tacklind et al. |
| 5,628,209 A | 5/1997 | Brown |
| 5,692,906 A | 12/1997 | Corder |
| 5,704,922 A | 1/1998 | Brown |
| 5,720,733 A | 2/1998 | Brown |
| 5,722,418 A | 3/1998 | Brown |
| 5,730,654 A | 3/1998 | Brown |
| 5,772,586 A | 6/1998 | Heinonen et al. |
| 5,782,814 A | 8/1998 | Brown et al. |
| 5,792,117 A | 8/1998 | Brown |
| 5,794,219 A | 8/1998 | Brown |
| 5,822,715 A | 10/1998 | Worthington et al. |
| 5,828,943 A | 10/1998 | Brown |
| 5,832,448 A | 11/1998 | Brown |
| 5,879,163 A | 3/1999 | Brown et al. |
| 5,887,133 A | 3/1999 | Brown et al. |
| 5,897,493 A | 4/1999 | Brown |
| 5,899,855 A | 5/1999 | Brown |
| 5,902,234 A | 5/1999 | Webb |
| 5,913,310 A | 6/1999 | Brown |
| 5,918,603 A | 7/1999 | Brown |
| 5,933,136 A | 8/1999 | Brown |
| 5,940,801 A | 8/1999 | Brown |
| 5,941,829 A | 8/1999 | Saltzstein |
| 5,951,300 A | 9/1999 | Brown |
| 5,956,501 A | 9/1999 | Brown |
| 5,960,403 A | 9/1999 | Brown |
| 5,967,975 A | 10/1999 | Ridgeway |
| 5,977,059 A | 11/1999 | Khoo |
| 5,985,559 A | 11/1999 | Brown |
| 5,997,476 A | 12/1999 | Brown |
| 6,023,686 A | 2/2000 | Brown |
| 6,024,699 A | 2/2000 | Surwit et al. |
| 6,032,119 A | 2/2000 | Brown et al. |
| 6,068,615 A | 5/2000 | Brown et al. |
| 6,101,478 A | 8/2000 | Brown |
| 6,110,148 A | 8/2000 | Brown et al. |
| 6,113,578 A | 9/2000 | Brown |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,186,145 B1 | 2/2001 | Brown |
| 6,196,970 B1 | 3/2001 | Brown |
| 6,210,272 B1 | 4/2001 | Brown |
| 6,231,519 B1 | 5/2001 | Blants et al. |
| 6,233,539 B1 | 5/2001 | Brown |
| 6,234,964 B1 | 5/2001 | Iliff et al. |
| 6,240,393 B1 | 5/2001 | Brown |
| 6,246,992 B1 | 6/2001 | Brown |
| 6,248,065 B1 | 6/2001 | Brown |
| 6,260,022 B1 | 7/2001 | Brown |
| 6,270,455 B1 | 8/2001 | Brown |
| 6,302,844 B1 | 10/2001 | Walker et al. |
| 6,330,426 B2 | 12/2001 | Brown et al. |
| 6,334,778 B1 | 1/2002 | Brown |
| 6,352,523 B1 | 3/2002 | Brown et al. |
| 6,368,273 B1 | 4/2002 | Brown |
| 6,375,469 B1 | 4/2002 | Brown |
| 6,375,614 B1 | 4/2002 | Braun et al. |
| 6,379,301 B1 | 4/2002 | Worthington et al. |
| 6,381,577 B1 | 4/2002 | Brown |
| 6,402,691 B1 | 6/2002 | Peddicord et al. |
| 6,409,660 B1 | 6/2002 | Sjogvist et al. |
| 6,416,471 B1 | 7/2002 | Kumar et al. |
| 6,418,346 B1 | 7/2002 | Nelson et al. |
| 6,454,705 B1 | 9/2002 | Cosentino et al. |
| 6,482,156 B2 | 11/2002 | Iliff et al. |
| 6,565,509 B1 | 5/2003 | Say et al. |
| 6,579,231 B1 | 6/2003 | Phipps |
| 6,602,191 B2 | 8/2003 | Quy |
| 6,610,010 B2 | 8/2003 | Sjogvist et al. |
| 6,610,012 B2 | 8/2003 | Mault et al. |
| 6,645,142 B2 | 11/2003 | Braig et al. |
| 6,669,631 B2 | 12/2003 | Norris et al. |
| 6,675,030 B2 | 1/2004 | Ciurczak et al. |
| 6,694,177 B2 | 2/2004 | Eggers et al. |
| 6,699,188 B2 | 3/2004 | Wessel |
| 6,723,045 B2 | 4/2004 | Cosentino et al. |
| 6,723,046 B2 | 4/2004 | Lichtenstein et al. |
| 6,783,492 B2 | 8/2004 | Dominguez et al. |
| 6,804,558 B2 | 10/2004 | Haller et al. |
| 6,820,057 B1 | 11/2004 | Loch et al. |
| 6,840,904 B2 | 1/2005 | Goldberg |
| 6,849,045 B2 | 2/2005 | Iliff |
| 6,885,544 B2 | 3/2005 | Austin |
| 6,875,174 B2 | 4/2005 | Braun et al. |
| 6,891,936 B2 | 5/2005 | Kai et al. |
| 6,893,396 B2 | 5/2005 | Schulze et al. |
| 6,920,360 B2 | 7/2005 | Lee et al. |
| 6,936,007 B2 | 8/2005 | Quy |
| 6,955,646 B2 | 10/2005 | Christ et al. |
| 6,968,375 B1 | 11/2005 | Brown et al. |
| 6,976,958 B2 | 12/2005 | Quy |
| 6,985,762 B2 | 1/2006 | Brashears et al. |
| 7,077,806 B2 | 7/2006 | Ackermann et al. |
| 7,104,955 B2 | 9/2006 | Bardy |
| 7,130,396 B2 | 10/2006 | Rogers et al. |
| 7,156,808 B2 | 1/2007 | Quy |
| 7,156,809 B2 | 1/2007 | Quy |
| 7,167,818 B2 | 1/2007 | Brown |
| 7,188,151 B2 | 3/2007 | Kumar et al. |
| 7,223,235 B2 | 5/2007 | Brown |
| 7,223,236 B2 | 5/2007 | Brown |
| 7,252,636 B2 | 8/2007 | Brown |
| 7,258,666 B2 | 8/2007 | Brown |
| 7,260,480 B1 | 8/2007 | Brown et al. |
| 7,264,591 B2 | 9/2007 | Brown |
| 7,277,867 B1 | 10/2007 | Brown et al. |
| 7,297,109 B2 | 11/2007 | Brown |

(56) References Cited

U.S. PATENT DOCUMENTS

| | | |
|---|---|---|
| 7,305,348 B1 | 12/2007 | Brown |
| 7,310,668 B2 | 12/2007 | Brown |
| 7,320,030 B2 | 1/2008 | Brown |
| 7,321,920 B2 | 1/2008 | Washburn |
| 7,392,167 B2 | 1/2008 | Brown |
| 7,340,503 B2 | 3/2008 | Washburn |
| 7,353,258 B2 | 4/2008 | Washburn |
| 7,399,276 B1 | 7/2008 | Brown et al. |
| 2001/0011224 A1 | 8/2001 | Brown |
| 2001/0016310 A1 | 8/2001 | Brown et al. |
| 2001/0039373 A1 | 11/2001 | Cunningham et al. |
| 2001/0047252 A1 | 11/2001 | Brown |
| 2001/0049096 A1 | 12/2001 | Brown |
| 2002/0016719 A1 | 2/2002 | Nemeth et al. |
| 2002/0019748 A1 | 2/2002 | Brown |
| 2002/0026223 A1 | 2/2002 | Riff et al. |
| 2002/0039373 A1 | 4/2002 | Ishimaru |
| 2002/0052539 A1 | 5/2002 | Haller et al. |
| 2002/0111541 A1 | 8/2002 | Bibl et al. |
| 2002/0120310 A1 | 8/2002 | Linden et al. |
| 2002/0128866 A1* | 9/2002 | Goetzke ............... G16H 50/50 705/2 |
| 2002/0133377 A1 | 9/2002 | Brown |
| 2003/0009088 A1 | 1/2003 | Korth et al. |
| 2003/0036683 A1 | 2/2003 | Kehr et al. |
| 2003/0072424 A1 | 4/2003 | Evans et al. |
| 2003/0088290 A1 | 5/2003 | Spinelli et al. |
| 2003/0163351 A1 | 8/2003 | Brown et al. |
| 2003/0166994 A1 | 9/2003 | Ooshima et al. |
| 2003/0208113 A1 | 11/2003 | Mault |
| 2003/0212579 A1 | 11/2003 | Brown et al. |
| 2003/0229514 A2 | 12/2003 | Brown |
| 2004/0019259 A1 | 1/2004 | Brown et al. |
| 2004/0044272 A1 | 3/2004 | Moerman et al. |
| 2004/0054263 A1 | 3/2004 | Moerman et al. |
| 2004/0102683 A1 | 5/2004 | Khanuja et al. |
| 2004/0102685 A1 | 5/2004 | Cosentino et al. |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0122297 A1 | 6/2004 | Stahmann et al. |
| 2004/0133080 A1 | 7/2004 | Mazar et al. |
| 2004/0176666 A1 | 9/2004 | Chait |
| 2004/0215492 A1 | 10/2004 | Choi |
| 2004/0236189 A1 | 11/2004 | Hawthorne et al. |
| 2004/0236199 A1 | 11/2004 | Hawthorne et al. |
| 2004/0249250 A1 | 12/2004 | Mcgee et al. |
| 2005/0003470 A1 | 1/2005 | Nelson et al. |
| 2005/0010087 A1 | 1/2005 | Banet et al. |
| 2005/0059895 A1 | 3/2005 | Brown |
| 2005/0060194 A1 | 3/2005 | Brown |
| 2005/0065815 A1 | 3/2005 | Mazar et al. |
| 2005/0075542 A1 | 4/2005 | Goldreich |
| 2005/0080322 A1 | 4/2005 | Korman |
| 2005/0080652 A1 | 4/2005 | Brown |
| 2005/0086083 A1 | 4/2005 | Brown |
| 2005/0113655 A1 | 5/2005 | Hull |
| 2005/0197553 A1 | 9/2005 | Cooper |
| 2005/0216199 A1 | 9/2005 | Benet |
| 2005/0228883 A1 | 10/2005 | Brown |
| 2005/0234307 A1 | 10/2005 | Heinonen et al. |
| 2005/0235060 A1 | 10/2005 | Brown |
| 2005/0240111 A1 | 10/2005 | Chung |
| 2005/0273509 A1 | 12/2005 | Brown |
| 2005/0283385 A1* | 12/2005 | Hunkeler ............... G16H 10/60 705/2 |
| 2006/0004611 A1 | 1/2006 | Brown |
| 2006/0009684 A1 | 1/2006 | Kim |
| 2006/0009697 A1 | 1/2006 | Banet et al. |
| 2006/0009705 A1 | 1/2006 | Brown |
| 2006/0009706 A1 | 1/2006 | Brown |
| 2006/0010014 A1 | 1/2006 | Brown |
| 2006/0017563 A1 | 1/2006 | Rosenfeld et al. |
| 2006/0022834 A1 | 2/2006 | Rosenfeld et al. |
| 2006/0025657 A1 | 2/2006 | Rosenfeld et al. |
| 2006/0036134 A1 | 2/2006 | Tarassenko et al. |
| 2006/0036619 A1 | 2/2006 | Fuerst |
| 2006/0074338 A1 | 4/2006 | Greenwald et al. |
| 2006/0080152 A1 | 4/2006 | Brown |
| 2006/0089542 A1 | 4/2006 | Sands |
| 2006/0089969 A1 | 4/2006 | Brown |
| 2006/0100910 A1 | 5/2006 | Brown |
| 2006/0129432 A1 | 6/2006 | Choi et al. |
| 2006/0142648 A1 | 6/2006 | Banet et al. |
| 2006/0155582 A1 | 7/2006 | Brown |
| 2006/0167345 A1 | 7/2006 | Vespasiani |
| 2006/0167346 A1 | 7/2006 | Sarel |
| 2006/0173260 A1 | 8/2006 | Gaoni et al. |
| 2006/0173715 A1 | 8/2006 | Wang |
| 2006/0178914 A1 | 8/2006 | Brown |
| 2006/0189853 A1 | 8/2006 | Brown |
| 2006/0212316 A1 | 9/2006 | Jackson et al. |
| 2006/0234202 A1 | 10/2006 | Brown |
| 2006/0235722 A1 | 10/2006 | Brown |
| 2006/0241975 A1 | 10/2006 | Brown |
| 2006/0247951 A1 | 11/2006 | Brown |
| 2006/0252089 A1 | 11/2006 | Brown |
| 2006/0253296 A1 | 11/2006 | Liisberg et al. |
| 2006/0253303 A1 | 11/2006 | Brown |
| 2006/0253574 A1 | 11/2006 | Brown |
| 2006/0253576 A1 | 11/2006 | Brown |
| 2006/0259201 A1 | 11/2006 | Brown |
| 2006/0259332 A1 | 11/2006 | Brown |
| 2006/0271214 A1 | 11/2006 | Brown |
| 2006/0271404 A1 | 11/2006 | Brown |
| 2006/0285660 A1 | 12/2006 | Brown |
| 2006/0285736 A1 | 12/2006 | Brown |
| 2006/0287883 A1* | 12/2006 | Turgiss ............... G06Q 30/0241 705/2 |
| 2006/0287889 A1 | 12/2006 | Brown |
| 2006/0287931 A1 | 12/2006 | Brown |
| 2006/0293571 A1 | 12/2006 | Bao et al. |
| 2006/0293607 A1 | 12/2006 | Alt et al. |
| 2006/0294233 A1 | 12/2006 | Brown |
| 2007/0010719 A1 | 1/2007 | Huster et al. |
| 2007/0011320 A1 | 1/2007 | Brown |
| 2007/0016445 A1 | 1/2007 | Brown |
| 2007/0016446 A1 | 1/2007 | Brown |
| 2007/0016447 A1 | 1/2007 | Brown |
| 2007/0018448 A1 | 1/2007 | Brown |
| 2007/0021984 A1 | 1/2007 | Brown |
| 2007/0032997 A1 | 2/2007 | Brown |
| 2007/0048691 A1 | 3/2007 | Brown |
| 2007/0055486 A1 | 3/2007 | Brown |
| 2007/0060796 A1 | 3/2007 | Kim |
| 2007/0061167 A1 | 3/2007 | Brown |
| 2007/0067251 A1 | 3/2007 | Brown |
| 2007/0068539 A1 | 3/2007 | Hall et al. |
| 2007/0076681 A1 | 4/2007 | Brown |
| 2007/0094049 A1 | 4/2007 | Brown |
| 2007/0094353 A1 | 4/2007 | Brown |
| 2007/0100665 A1 | 5/2007 | Brown |
| 2007/0100932 A1 | 5/2007 | Brown |
| 2007/0100934 A1 | 5/2007 | Brown |
| 2007/0118348 A1 | 5/2007 | Brown |
| 2007/0118403 A1 | 5/2007 | Brown |
| 2007/0118404 A1 | 5/2007 | Brown |
| 2007/0118588 A1 | 5/2007 | Brown |
| 2007/0118589 A1 | 5/2007 | Brown |
| 2007/0124179 A1 | 5/2007 | Brown |
| 2007/0124466 A1 | 5/2007 | Brown |
| 2007/0135688 A1 | 6/2007 | Brown |
| 2007/0156457 A1 | 7/2007 | Brown |
| 2007/0156892 A1 | 7/2007 | Brown |
| 2007/0156893 A1 | 7/2007 | Brown |
| 2007/0168226 A1 | 7/2007 | Brown |
| 2007/0168242 A1 | 7/2007 | Brown |
| 2007/0168504 A1 | 7/2007 | Brown |
| 2007/0179352 A1 | 8/2007 | Randlov et al. |
| 2007/0212671 A1 | 9/2007 | Brown |
| 2007/0213603 A1 | 9/2007 | Brown |

(56) References Cited

U.S. PATENT DOCUMENTS

2007/0213604 A1 9/2007 Brown
2007/0213605 A1 9/2007 Brown
2007/0213608 A1 9/2007 Brown
2007/0287895 A1 12/2007 Brown

OTHER PUBLICATIONS

Lehmann et al., "AIDA$^2$ : A Mk. II Automated Insulin Dosage Advisor," Journal of Biomedical Engineering, Butterworth, Guildford, GB, vol. 15, No. 3, May 1, 1993, pp. 201-211.
Deutsch T et al., "Utopia: A Consultation System for Visit-by-Visit Diabetes Management," Medical Infomatica, Taylor and Francis, Basingstoke. GB, vol. 21, No, 4, Oct. 1, 1996, pp. 345-358.
Steil G. M. et al., "Modeling insulin Action for Development of a Closed-Loop Artificial Pancreas," Diabetes Technology and Therapeutics, Mary Ann Liebert, Larchmont, NY, vol. 7, No. 1, Feb. 1, 2005, pp. 94-109.
Boutayeb A. et al., "A critical reviewk of Mathematical Models and Data Used in Diabetology," Biomedical Engineering Online, Biomed Central Ltd., London, England, vol. 5. No. 1, Jun. 29, 2006.
Rune V. Overgaard et al., "Mathematical Beta Cell Model for Insulin Secretion Following IVGTT and OGTT," Annals of Biomedical Engineering, Kluwer Academic Publishers-Plenum Publishers, NE, vol. 34, No. 8, Jul. 13, 2006.
Minor J. M. et al., "Analysis of Clinical Data Using Neural Nets," Journal of Biopharmaceutical Statistics, Mar. 1996, vol. 6, No. 1, Mar. 1996.
Written Opinion of the International Searching Authority issued by the European Patent Office dated Jul. 17, 2008.

\* cited by examiner

SYSTEMS AND METHODS FOR DISEASE CONTROL AND MANAGEMENT

RELATED APPLICATION(S)

This application is a continuation of U.S. application Ser. No. 16/186,996, filed on Nov. 12, 2018, which is a continuation of U.S. application Ser. No. 15/670,551, filed on Aug. 7, 2017, which is a continuation of U.S. application Ser. No. 12/071,486, filed on Feb. 21, 2008, now U.S. Pat. No. 9,754,077, which claims the benefit of priority to U.S. Provisional Application No. 60/902,490, filed on Feb. 22, 2007, all of which are incorporated herein by reference, in their entireties.

TECHNICAL FIELD

The present invention generally relates to the field of disease management. More particularly, and without limitations, the invention relates to systems and methods for disease management by providing treatment recommendations and information based on relevant data collected about a patient.

BACKGROUND

Generally speaking, disease management refers to a wide range of activities that may affect a patient's health status. These activities include programs to improve a patient's compliance with their treatment regimen, and helping the patient adjust their regimen according to evidence-based treatment guidelines. The goal of these programs is to attempt to maintain or improve the patient's health status and quality of life, and to reduce the total costs of health care.

One approach is to identify and provide a variety of appropriate services to patients that are suitable for a certain program. Examples of such services include periodic phone calls to a patient to monitor the status of the patient, personalized goal-oriented feedback on the patient's self care, access to nurse call centers, and educational materials. Some of these programs attempt to modify services based on data obtained from the patient's self reports and administrative claims. These programs attempt to help patients identify regimens, manage their symptoms, self-monitor their conditions, and comply with their treatment. The drawbacks of this type of approach include the enormous resources necessary to provide these human-based services, and the lack of timely, appropriate, and accurate patient data to provide appropriate services. For example, a single case manager can only assist a limited number of patients. As a result, such a case manager may, for example, be able to contact a patient only once a month and may be forced to rely on out-dated data for the patient.

An alternative approach for disease management is to use a system that provides corrective action to a patient based on limited information provided by the patient. For example, a diabetes patient can provide their current glucose value using an electronic patient-operated apparatus, and the system can recommend a corrective action to the patient based on the application of formulas well known in the art. A corrective action can be either administration of an extra insulin dose or consumption of carbohydrates. A drawback of this approach is that it fails to provide customized disease management for each individual patient. Similarly, the formulas that can be applied for any patient part of the general population do not take into account the complete dynamics of a particular's patient's disease and the corrective actions advised to a patient are limited. As a result, a patient is denied the optimal treatment recommendations that can only be targeted for a particular patient. Finally, the success of the system is wholly dependent on a proactive and conscientious patient.

In view of the foregoing, there is a need for an improved solution for disease management. In particular, there is a need for systems and methods for effective disease management that can develop recommendations for a patient based on the particular patient's data.

SUMMARY

The present invention provides methods, computer-readable media, and systems for providing disease management. This is achieved by providing treatment recommendations targeted for a particular patient based on the patient's data.

In one exemplary embodiment, a system is provided including, for example, an input device for receiving patient data; a transmitter for transmitting the received patient data from the input device; and a disease management server. The disease management server may include a receiver for receiving the transmitted patient data, a processor for developing a treatment recommendation, and an output device for outputting the treatment recommendation. The processor may develop treatment recommendations by executing a basic model of the physiological system of the patient to generate a modified model for the patient based on the patient data, performing a statistical analysis of the patient data to detect data excursions of the parameter values, using the modified model to determine factors causing the data excursions, and using the model to develop a treatment recommendation to ameliorate negative effects of the disease. The patient data may include but is not limited to the following parameters: patient carbohydrate intake, patient medication doses, blood glucose level, activity of the patient, and the corresponding time and optional context for the data.

The processor in the disease management server of the exemplary system may generate a plurality of treatment recommendations, including, for example, recommendations for dosing and timing of medication, and for patient dietary behavior. Executing the model comprises applying an algorithm to the patient data in a current state in conjunction with auxiliary patient data including, for example, patient blood lipid level, blood pressure, age, gender, height and weight, and race. The processor may be further configured to develop recommendations for collection of the patient data to improve the model, wherein the collection recommendations comprise recommendations for timing of blood glucose measurement. The processor may be further configured to perform statistical analysis employing a statistical design of experiments methodology and multivariate analyses to identify the factors causing the data excursions.

In another embodiment, the treatment recommendations may be developed at predetermined intervals, which may be determined based on a most-recent patient data collection time. The treatment recommendations may include a recommended time and dose of medication, including recommended combinations of available medications. The treatment recommendations may also include a recommended time and amount of carbohydrate intake.

In another alternate embodiment, the input device may be a patient-interactive interface operated by the patient. The system may include a portable device configured to operate the patient-interactive interface and the transmitter, wherein the transmitter transmits signals over a wireless communication to the disease management server. The system may also include a physician interface operable to receive information about the patient from the disease management server.

In another alternate embodiment, the patient data may be calibrated at a plurality of reading points to provide more information on pharmacokinetic/pharmacodynamic interactions of the patient.

In another alternate embodiment, generating the modified model may include utilizing equations that simulate interaction of primary factors effecting rate of change of the blood glucose of the patient, wherein the primary factors are calculated based on the patient data. The primary factors may include rate of digestion of the patient carbohydrate intake, cellular uptake of blood glucose by the patient, and impact of glucose inventory in liver, skeletal muscle, and fat tissues of the patient. The equation for the cellular uptake is a function of the blood glucose level, level of insulin acting as a catalyst, resistance factors, and digestive-activated hormones, and wherein the level of insulin is calculated based on the patient medication doses, patient pancreatic production, and insulin kinetics.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate embodiments and aspects of the present invention. In the drawings.

DESCRIPTION OF THE EMBODIMENTS

Figure 1:
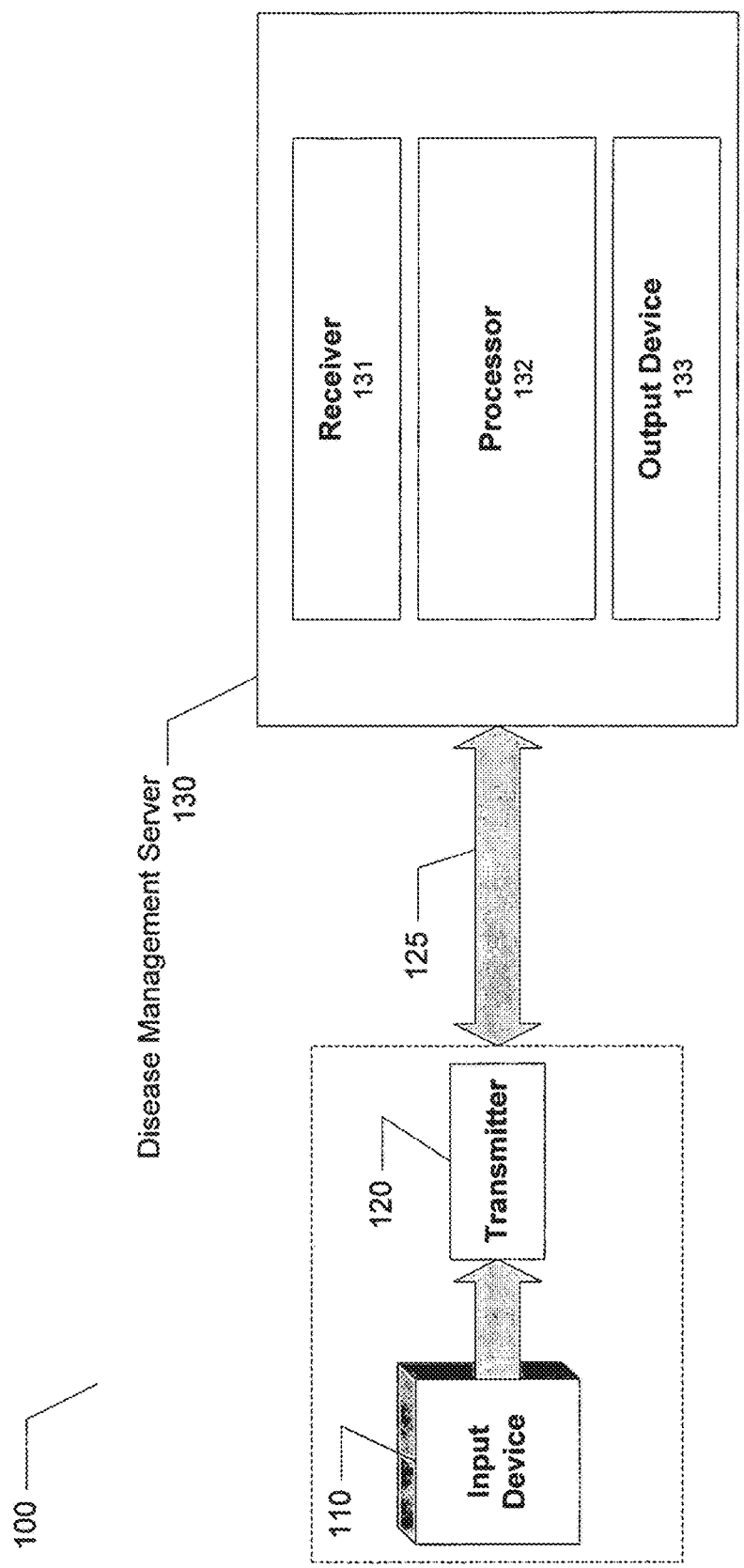
FIG. 1 illustrates an exemplary system, consistent with an embodiment of the invention.

The following detailed description refers to the accompanying drawings. Wherever possible, the same reference numbers are used in the drawings and the following description to refer to the same or similar parts. While several exemplary embodiments and features of the invention are described herein, modifications, adaptations and other implementations are possible, without departing from the spirit and scope of the invention. For example, substitutions, additions, or modifications may be made to the components illustrated in the drawings, and the exemplary methods described herein may be modified by substituting, reordering, or adding steps to the disclosed methods. Accordingly, the following detailed description does not limit the invention. Instead, the proper scope of the invention is defined by the appended claims.

FIG. 1 illustrates components of an exemplary system 100, consistent with an embodiment of the present invention. The two main components of the system are an input device 110 and a disease management server 130. A transmitter 120 may be a separate component or part of the input device. Transmitter 120 may include a modem to transmit information collected by input device 110 to disease management server 130. Transmitter 120 may also be used to receive information from disease management server 130 to provide to the user through the input device 110. For example, disease management server 130 may send information regarding what data it needs input device 100 collect from the patient.

Input device 110 and the transmitter 120 may be part of a single computer system. Alternatively, the transmitter may be on an intermediary computer system between the input device 110 and the disease management server 130. The transmitter 120 may serve as the intermediary for communication between the input device 110 and the disease management server. The components 110, 120, 130 may communicate with each over a communication medium 125. The communication medium may be any desired type of communication channel, including (but not limited to) the public switched telephone network (VSTN), cellular channel, other wireless channel, internal computer bus, intranet, internet, etc.

The input device 110 may be used to collect variety of patient data in a variety of ways. The input device 110 may be connected to one or more biometric measurement devices to collect biometric data. The biometric measurement devices may be implanted in the patient, connected to the patient, and/or completely external. A biometric measurement device may be part of or connected to the input device 110, or it may be a stand-alone device. A stand-alone biometric measurement device may communicate wirelessly with the input device 110. Examples of biometric measurement devices include, but are not limited to, scales, external blood pressure monitors, cardiac data sensors, implantable blood glucose sensors for continuous sensing, external blood glucose monitors, etc.

The input device 110 may also receive information from devices for administering medication. For example, the input device 110 may be connected to an insulin-delivery device. The input device 110 may receive information detailing the insulin doses a patient has taken from the insulin-delivery device and the times of dose administration.

The input device 110 may also receive information from other ancillary devices to collect a variety of information about the patient's behavior and status. For example, the input device 110 may be connected to a pedometer worn by the patient or exercise equipment used by the patient to track the physical activity of the patient. The input device 110 may be connected to a GPS system to track the movement and location of the patient. The input device may also be connected to a device that keeps track of a patient's dietary behavior.

The input device 110 may also receive information by having the patient enter particular information. The disease management server 130 may send request for particular information to be entered by the patient using the input device 110. The input device 110 may prompt the user to enter the particular information. The request sent by the disease management server 130 may be in the form of surveys designed to collect particular information. The surveys may be targeted to collect information about a patient's dietary behavior (e.g., carbohydrate intake, portion control), self-monitoring of blood glucose, medication doses, physical activity, psychological status, alcohol intake, smoking activity, and any other information that might effect the patient's well being. The input device 110 may prompt the patient to enter information by displaying the survey and receiving the patient's responses to the questions posed in the survey. The scripts may also be designed to educate the patient or to promote positive behavior/behavior modification by the patient.

The transmitter 120 may send the patient data collected by the input device 110 to the disease management server 130 immediately after the data is entered into the input device 110 by the patient.

As shown in FIG. 1, disease management server 130 may include a receiver 131, a processor 132, and an output device 133. The receiver 131 may receive patient data from the transmitter 120. The processor 132 may execute a program for generating/maintaining a modified model for a patient and developing treatment recommendations for the patient using the model based on the patient data. The output device 133 may output information to either the patient, a third party health care provider, or a remote device based on the treatment recommendations developed by the processor 132.

The processor 132 may generate a modified model for the patient based on the patient data the disease management server 130 receives through the receiver 131. The modified model may be used to estimate impact of a change in the patient's regimen (e.g., medication, food intake, physical activity) on the physiological system of the patient. The processor may generate a modified model for the patient by executing a basic model. A basic model models a physiological system of a patient based on established knowledge of disease dynamics and factors. The patient data is used to generate the modified model for a particular patient. The modified model can provide guidance to improve the patient's regimen and to gain a better understanding of how a particular patient is being affected by a disease dynamic. The use of patient data over an extended period of time allows the modification and improvements of the modified model as more data is collected for a particular patient. The modified model may also be used even when limited/incomplete patient data is received.

After the generation of a modified model, the processor 132 may perform a statistical analysis of patient data to detect data excursions. A data excursion is an event in which a value of a parameter (e.g., blood glucose level) is outside the normal/expected range for the parameter. The processor 132 may use the modified model it generated to determine the factors causing the data excursions and the effects of such data excursions. The modified model may then be used to develop a plurality of treatment recommendations to ameliorate negative effects of the disease. The output device 133 within the disease management server 130 may output information based on the treatment recommendations to the patient, a device relate to the patient, or a third party.

Figure 2:
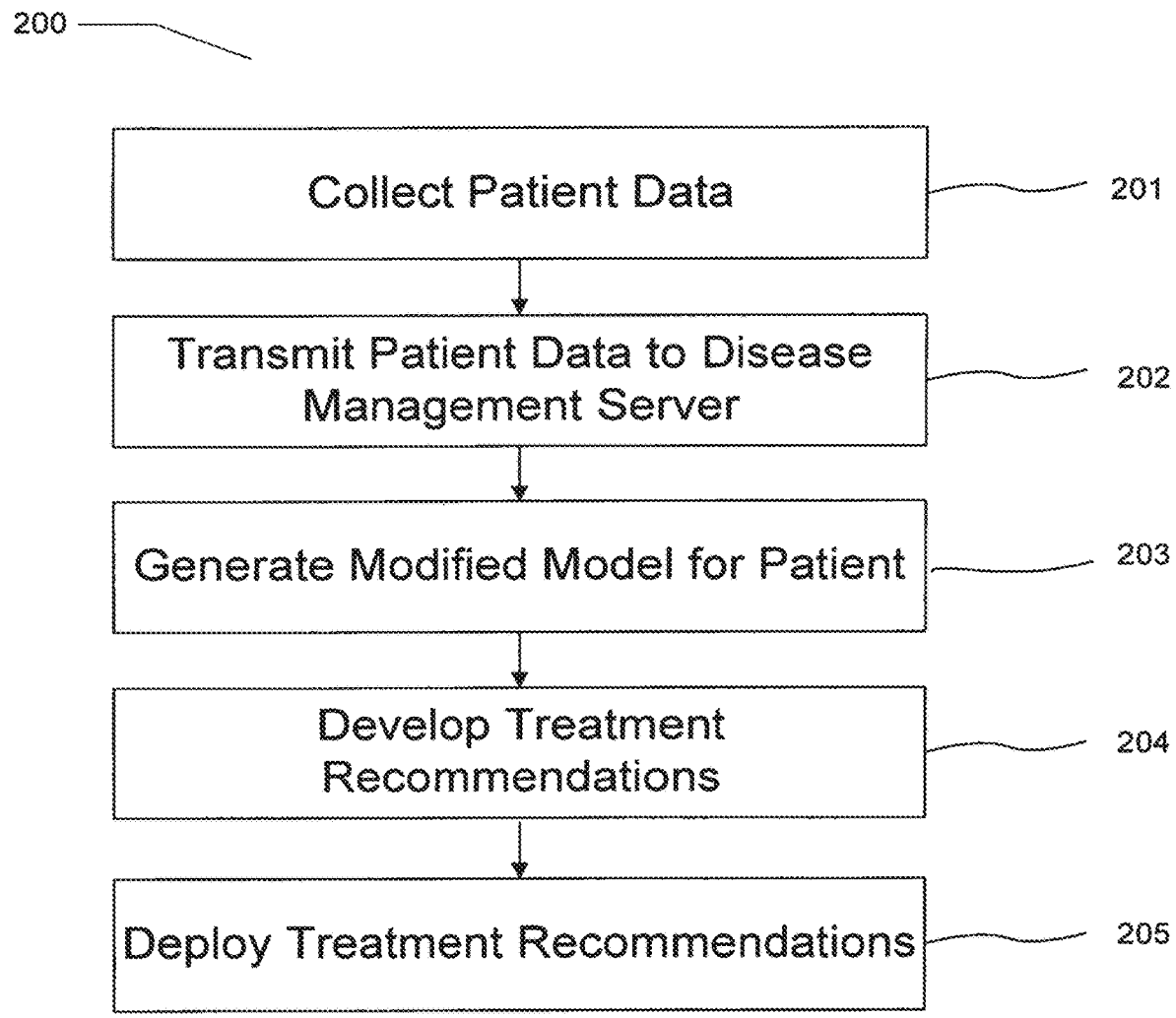
FIG. 2 is a flowchart of an exemplary method, consistent with an embodiment of the present invention.

FIG. 2 is a flowchart of an exemplary method 200, consistent with an embodiment of the present invention. Method 200 may be executed on a system illustrated in FIG. 1. According to the method, at step 201, the input device 110 may collect patient data. At step 202, the transmitter 120 may transmit the patient data to the disease management server 130. At step 203, the disease management server 130 may generate a modified model for the patient. At step 204 the disease management server 130 may develop treatment recommendations for the patient using the modified model generated at step 203. At step 205 the disease management server 130 may deploy treatment recommendations developed at step 204, by using the output device 133.

Figure 3:
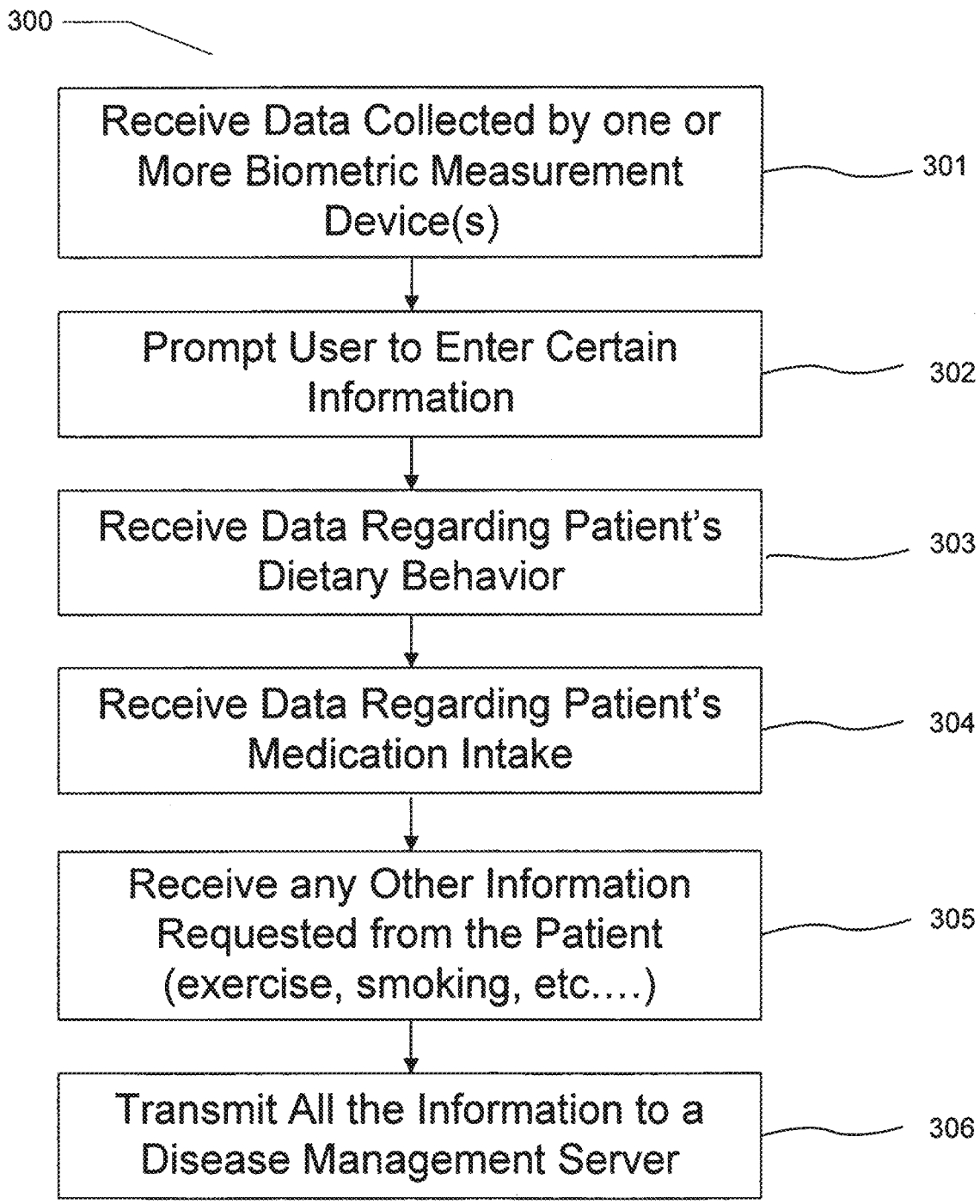
FIG. 3 is a flowchart of an exemplary method for collecting patient data, consistent with an embodiment of the present invention.

FIG. 3 is a flowchart of another exemplary method 300, consistent with an embodiment of the present invention. Method 300 depicts an example of an input device 110 receiving patient data. Steps 301, 303, 304, 305 of this method may be performed in no particular order. Steps 301, 303, 304, 305 present a limited set of examples of the different patient data that can be collected and how it may be collected by an input device 110.

At step 301, the input device 110 may receive data collected by one or more biometric measurement devices. The input device 110 may receive the data collected by one or more biometric measurement devices every time a measurement occurs by the biometric measurement device, at a certain predetermined interval, or when the input device is prompted to collect the biometric measurement data. Alternatively, as discussed above, at step 301, the biometric measurement data may be entered by the patient into the input device 110.

At step 302, the input device may prompt the user to enter specific information pertaining to factors that can effect the well being of the patient. The patient may be prompted to enter such information by being asked a series of questions. The patient may receive reminders through the input device to enter certain type of information at a certain time. Step 302 may repeat several times to collect different types of data from the patient at steps 301, 303, 304, 305.

At step 303, the input device 110 may receive information about the patient's dietary behavior. This information may be simply entered by the patient on a regular basis using the input device. The patient may use a remote workstation to enter the information and have it transferred to the input device. The information may be entered in response to the prompt(s) at step 302. The information may be received from a device that can track a patient's dietary behavior. An example of such a device is a food/drink caloric intake calculator. The calculator may be implemented, for example, on a cell phone, and a patient may enter information regarding his/her dietary behavior into the cell phone. Alternatively, the calculator may be part of the input device. The information may also be received by the input device 110 from a restaurant where the patient eats. Another example is a camera-based food calculator. The input device 110 may be able to receive pictures of food eaten by the patient. Image recognition techniques may later be used to identify the food consumed by the patient, and determine the carbohydrate intake of the patient for example.

At step 304, the input device 110 may receive information about what medications the patient is taking, at what doses, and at what times. The patient may simply enter the information to be received by the input device independently, or the patient may enter the information in response to a prompt at step 302. The input device 110 may also be connected to other devices, and may receive information regarding the patient's medication intake from the other devices.

At step 305, the input device 110 may receive any other pertinent information from the patient that may assist successful disease management. This information may be received directly from the patient, a health care provider, a monitoring device, a third party, etc. A person can be prompted by the input device 110 to enter the information. Examples of information that may be collected may relate to the patient's exercise, smoking, alcohol intake, etc.

The input device 110 may also receive information from the patient at steps 301, 303, 304, and 305 regarding patients attitude towards modifying behavior that affects the respective data received at each step.

Figure 4:
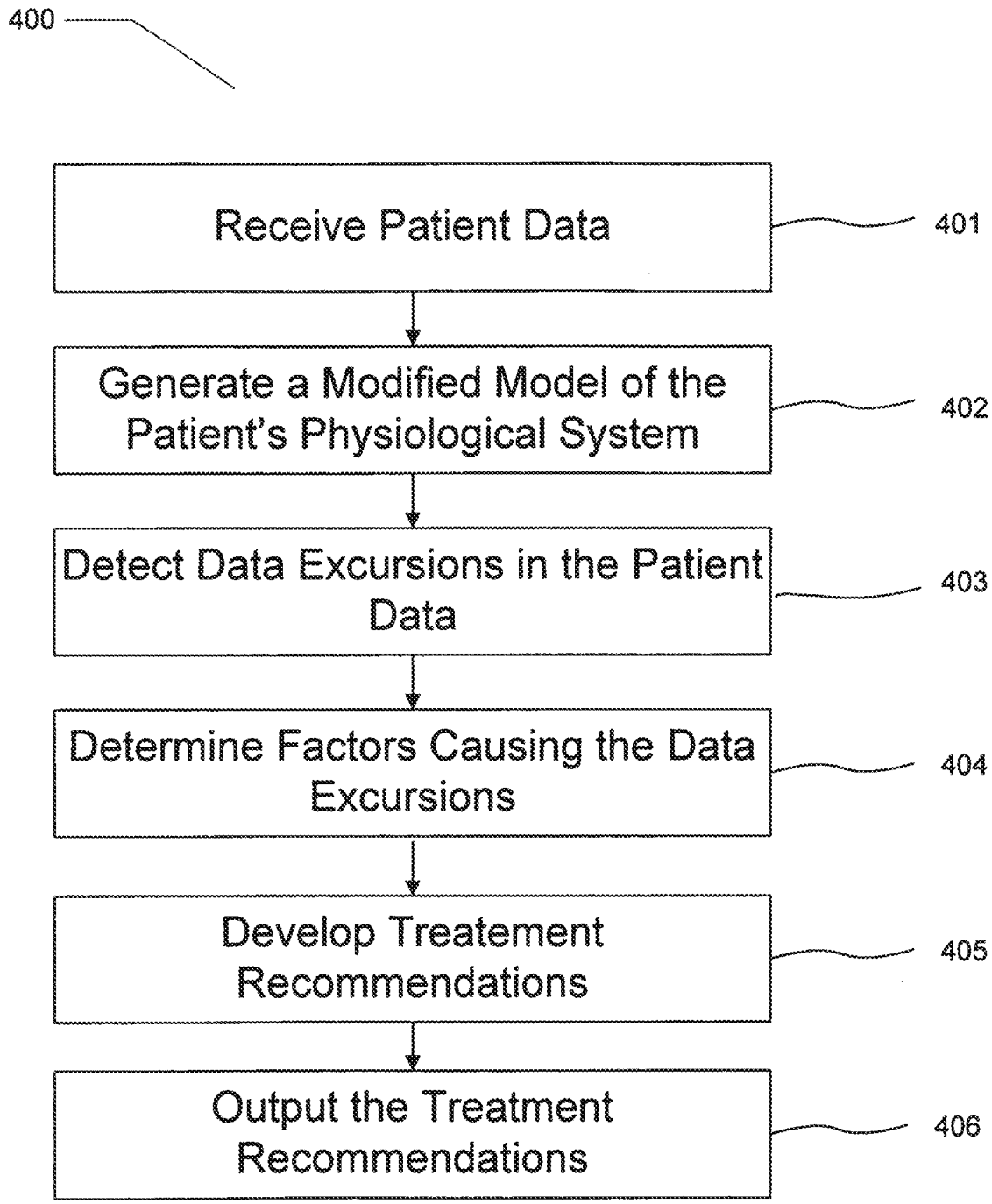
FIG. 4 depicts an example of a disease managements server developing treatment recommendations, consistent with an embodiment of the present invention.

FIG. 4 is a flowchart of another exemplary method 400, consistent with an embodiment of the present invention. Method 400 depicts an example of a disease management server 130 generating treatment recommendations for a patient. At step 401, a receiver 131 of the disease management server 130 receives patient data from a transmitter 120. The patent data is collected by input device 110 (see FIG. 3) and transmitted by transmitter 120 from the input device 110 to the disease management server 130. Steps 402, 403, 404, 405 may be performed by a processor 132 in the disease management server.

At step 402, the disease management server 130 uses the patient data to generate a modified model of the patient's physiological system. The modified model may be used to estimate the impact of a change of a certain factor (data) on the patient (other data). The modified model represents the effects of a change in different data on the particular patient's physiological system, and in turn how the physiological system of the patient effects the data. The modified model may be a previously generated modified model updated based on new patient data. The model is generated by executing a basic model based on the patient data (402). The basic model represents the minimal assumptions and parameters of a person's physiological system and the correlation of certain factors. How the factors interact and correlate is different for different patients. The patient data is used to adjust the basic model and generate a modified model for a particular patient. The more patient data is collected over time, the more accurate the modified model is for the particular patient. In addition, the collection of data from multiple patients may be used to improve the basic model.

At step 403, the disease management server 130 performs a statistical analysis to detect data excursions in the patient data. A data excursion may be indicated when certain data collected at a certain time is outside the normal range that can be expected for that data for the particular patient. For example, a data excursion may be a blood glucose measurement that is outside the normal blood glucose range for the particular patient.

At step 404, the disease management server 130 uses the modified model generated at step 402 to determine the factors causing the data excursions detected at step 403. For example, the disease management server 130 may determine if a change in amount of timing of medication or food intake of the patient caused the data excursion of blood glucose measurement.

At step 405, the disease management server 130 may develop treatment recommendations to ameliorate negative effects of the patient's disease. The disease management server 130 may use the modified model to determine the treatment recommendations which are optimal for the patient. For example, if a data excursion caused a negative effect on the patient, a treatment recommendation may be developed to prevent such a data excursion in the future. Examples of treatment recommendations may include adjusting food or medication intake, adjusting how and what data is collected, advising the patient to modify certain behaviors, providing educational materials to the patient, alerting the patient's health care provider, etc.

At step 406, the output device 133 of disease management server 130 may output the treatment recommendations developed at step 405. The treatment recommendations are transmitted to the appropriate party or device. For example, a treatment recommendation to increase the patient's insulin dose can be transmitted directly to the insulin-delivery device (pump). If, for example, the treatment recommendation is to collect certain additional data about the patient to provide optimal treatment recommendations in the future, a script can be transmitted to the patient through the input device 110 to collect the additional data at certain times.

Figure 5:
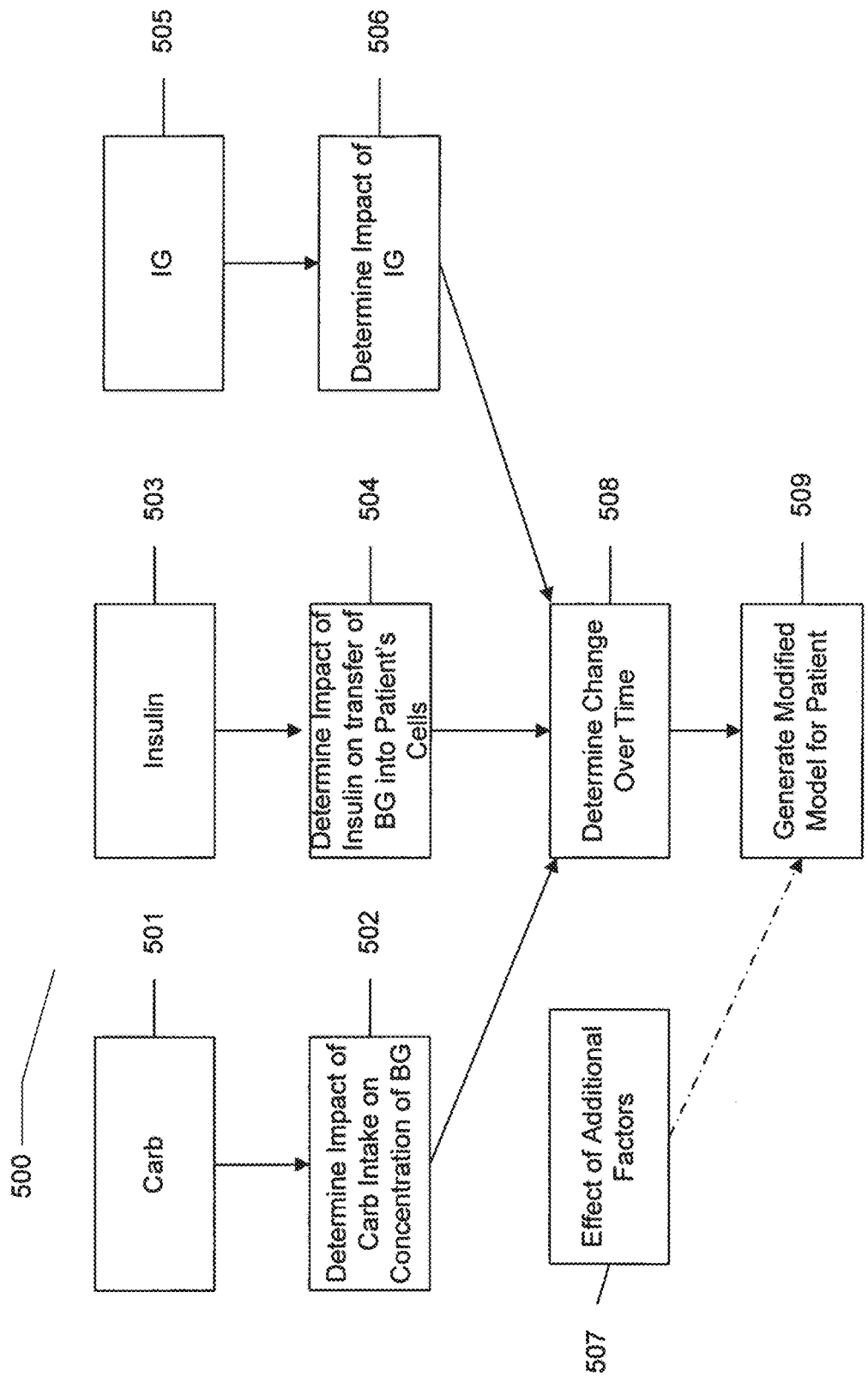
FIG. 5 is an exemplary diagram showing a generation of a modified model for a patient, consistent with an embodiment of the present invention.

FIG. 5 is an exemplary diagram showing a generation of a modified model for a patient, consistent with an embodiment of the present invention. The modified model is generated by the basic model. The diagram, in effect, is representing the basic model. The model in this embodiment focuses on the primary factors that impact the daily blood glucose (BC) of a patient: carbohydrate intake, insulin level of the patient, and glucose inventory of the patient. The model inherently includes within these primary factors the complex interactions of the hormonal-signaling network that supports the endocrine processes. First, it is necessary to determine the carbohydrate intake 501, insulin level 503, and glucose inventory 505 of the patient to generate the model. The patient data is used to determine the respective primary factors. The carbohydrate intake is determined based on the amount of carbohydrates ingested by the patient that become the primary source of blood glucose for the patient (501). The insulin level of the patient is determined on a variety of factors including dosing, pancreatic production, and kinetics (505, see FIG. 6 for further detail). The glucose inventory is determined based on the glucose stored in the liver, skeletal muscle, and fat tissues of the patient (506).

After determining the carbohydrate intake of the patient, an impact of the carbohydrate intake (carbs) on concentration of the blood glucose may be modeled (502). This may be modeled based on the following equation for instantaneous blood glucose concentration:

$$\frac{d[BG]}{dt} = \beta \frac{d[\text{carbs}, BG, \text{incretins}]}{dt},$$

wherein [BG] may be blood glucose (BG) concentration, [carbs] may be represented as a first order kinetics function of time (t), β may be for example about 5 BG units/carbohydrate unit, and incretins are the digestive-activated hormones of the patient.

The impact of insulin on transfer of blood glucose into patient's cells (504) is accounted for in the modified model. Insulin is accounted for as a catalyst, not as a compound that forms with blood glucose. The instantaneous rate decrease of blood glucose concentration from instantaneous insulin concentration in blood may be modeled based on the following equation:

$$-\frac{d[BG]}{dt} = \alpha(t) \times [BG][\text{insulin}],$$

wherein [insulin] may be the instantaneous insulin concentration in blood, α includes resistance impact of diabetes and is about 0.3 if rate is −50 BG units/insulin unit above BG of 140, and α(t) includes diurnal variations. Alternatively, α(t) may be approximated without any time dependence, using the 24 hour mean.

Finally, it is necessary to account for the impact of the glucose inventory (IG) on the blood glucose (BG) (506), where the glucose inventory absorbs blood glucose on storage and release blood glucose on retrieval (mass action kinetics). This may be modeled based on the following equation:

$$\frac{d[BG]}{dt} = -\frac{d[IG]}{dt},$$

where $$\frac{d[IG]}{dt} = -\gamma\left([IG] + \frac{\{-[BG] - [IG]\}}{\{1 + \exp(\omega\{\tau - \alpha[\text{insulin}]\})\}}\right),$$

wherein τ is the threshold; if resistant insulin is greater then the threshold, then blood glucose decreases by going into liver and fat as glucose storage (IG) and is not released through the liver. And wherein γ relates concentration of glucose to changes in IG. The IG functionality may be modeled by other similar forms at the conceptual level since the phenomenological description is incomplete.

The total change in blood glucose over a time interval (508) may be modeled based on the sum of the three factors 502, 504, 506 described above. The complete basic model may be based on the following equation (509):

$$\frac{d}{dt}BG(t) = \left[\left[\beta\left(\frac{d}{dt}\text{carbs}(t)\right) - \alpha \cdot BG(t) \cdot \text{insulin}(t)\right] - \frac{d}{dt}IG(t) + \text{errors}\right],$$

where the storage or release of blood glucose as mediated by resistant insulin may be expressed in the following equation:

$$\frac{d}{dt}IG(t) = -\gamma\left[IG(t) + \frac{(-BG(t) - IG(t))}{[1 + \exp[W \cdot (\tau \cdot B \cdot \text{insulin}(t)]]}\right],$$

wherein W is the switching rate (i.e., the rate that IG switches from intake mode to output mode of BG). Errors may account for any additional or unknown factors besides the primary factors (507). Statistical methods may be used to estimate model parameters and their expected variations for a patient.

The model can then be used to determine factors causing the data excursions 404. The relative contributions of the primary factors may vary over the 24 hour day, especially adjacent to meals and fasting events. For example, the fasting segments of the BG profile between meals would see little impact from the carbohydrates (502), and, if in addition, insulin levels are near their norm's as defined by its storage threshold, then insulin (504) becomes the dominant effect. Hence, this allows an estimation of the a parameter and the insulin profile of the patient based on the model. The dosing profile is known (503), and comparison with the estimated profile provides information on pancreatic activity. Under these conditions, one can also test if a changes among different fasting events. The testing can be accomplished through a treatment recommendation. The model provide a guide for timely regimen optimization for the particular patient. The optimization is based on a minimal-assumption model (MAM) that fits the major features in the data patterns of the patient. The MAM for BG data patterns may be expressed, for example, as follows: BG=MAM(t, injections, orals, digestion, diurnals, activity, liver processes, immune reaction, beta islets)+error.

Given α, one can estimate inventory parameters from the segments of the model capturing fasting events at non-normal levels of insulin. With these two sources established, one can now estimate the impact of carbohydrates during meals, since carbohydrates kinetics are known. Similarly, the MAM may be used to determine the effect on the patient's BG of changing other factors (ex. medications). A key feature of MAM is that it can model answers to "what if" questions for each individual patient given any scenario of lifestyle and treatment regimen/conditions over any interval of time both retrospectively and prospectively.

Figure 6:
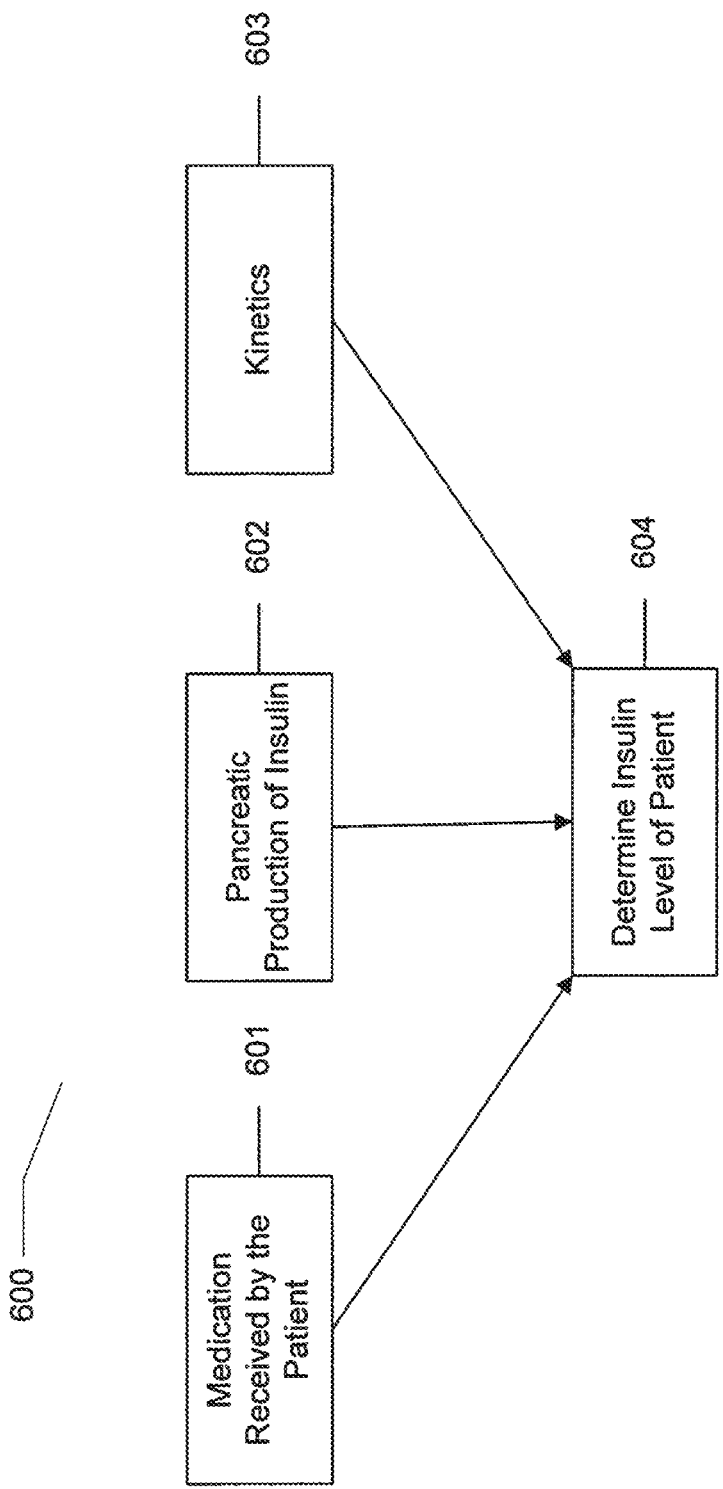
FIG. 6 is an exemplary diagram showing a determination of the insulin of a patient, consistent with an embodiment of the present invention.

FIG. 6 is a diagram showing a determination of the insulin of a patient (503), consistent with an embodiment of the present invention. The insulin of a patient may be calculated 604 based on the insulin from the medication received by the patient 601, the insulin produced by the patient's pancreatic beta cells 602, and mass action kinetics of insulin 603. The effect of mass action kinetics on insulin may be accounted for, based on the following formula: insulin(t)=D (dbeta [0.3 (t−0.5), 2.1, 7]+E), wherein D is the units of insulin dose received by the patient, and wherein E is the approximate equilibrium level of 24 hour SA insulin. Optionally, one may use kinetics models to create the insulin dosing profiles. The insulin profile may take into account the difference between long-acting and short-acting kinetics that vary based on the source of the insulin.

The foregoing description has been presented for purposes of illustration. It is not exhaustive and does not limit the invention to the precise forms or embodiments disclosed. Modifications and adaptations of the invention will be apparent to those skilled in the art from consideration of the specification and practice of the disclosed embodiments of the invention. For example, the described implementations include software, but systems and methods consistent with the present invention may be implemented as a combination of hardware and software or in hardware alone. Examples of hardware include computing or processing systems, including personal computers, servers, laptops, mainframes, micro-processors and the like. Additionally, although aspects of the invention are described for being stored in memory, one skilled in the art will appreciate that these aspects can also be stored on other types of computer-readable media, such as secondary storage devices, for example, hard disks, floppy disks, or CD-ROM, the Internet or other propagation medium, or other forms of RAM or ROM.

Computer programs based on the written description and methods of this invention are within the skill of an experienced developer. The various programs or program modules can be created using any of the techniques known to one skilled in the art or can be designed in connection with existing software. For example, program sections or program modules can be designed in or by means of Java, C++, HTML, XML, or HTML with included Java applets. One or more of such software sections or modules can be integrated into a computer system or existing e-mail or browser software.

Moreover, while illustrative embodiments of the invention have been described herein, the scope of the invention includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps and/or inserting or deleting steps, without departing from the principles of the invention. It is intended, therefore, that the specification and examples be considered as exemplary only, with a true scope and spirit of the invention being indicated by the following claims and their full scope of equivalents.

What is claimed is:

1. An adaptive analytical behavioral health assistant system, comprising:
 a physical biometric measurement device configured to obtain biometric measurements from a user, and to wirelessly transmit the obtained biometric measurements, the physical biometric measurement device selected from one or more of a scale, an external blood pressure monitor, a cardiac data sensor, an implantable blood glucose sensor for continuous sensing, an external blood glucose monitor, a blood pressure measuring device for measuring blood pressure measurements of the user, or a weight measuring device for measuring weight measurements of the user; and
 a disease management server in wireless communication with the physical biometric measurement device, the disease management server including:
  a receiver for receiving the biometric measurements transmitted from the physical biometric measurement device; and
  one or more processors configured to:
   execute a basic model of a physiological system generic to any user to generate a modified model specific to a physiological system of the user, wherein generating the modified model comprises updating the basic model based on information specific to the physiological system of the user, wherein the modified model is configured to estimate an impact of a change in one or more factors on the physiological system of the user;
   execute the modified model to generate personalized notifications, based on the modified model;
   learning one or more effects of the received measurements on the physiological system, and updating an ability of the modified model to estimate an impact of further changes in the one or more factors on the physiological system of the user, thereby creating an updated modified model by machine learning;
   execute the updated modified model to generate updated personalized notifications; and
   output the personalized notifications and the updated personalized notifications to the physical biometric measurement device,
 wherein the physical biometric measurement device is further configured to receive the personalized notifications, modify an internal signal to output the personalized notifications and the updated personalized notifications to the user, such that the personalized notifications and the updated personalized notifications are formatted and provided to the user over a network when they are received at the physical biometric measurement device and wherein the personalized notifications or the updated personalized notifications comprise a treatment recommendation based on the physiological system of the user.

2. The system according to claim 1, wherein the receiver of the disease management server receives a measurement every time the physical biometric measurement device obtains a biometric measurement.

3. The system according to claim 1, wherein the receiver of the disease management server receives biometric measurements from the physical biometric measurement device at predetermined intervals.

4. The system according to claim 1, wherein the one or more processors of the disease management server are further configured to output an alert to a provider associated with the user.

5. The system according to claim 4, wherein the one or more processors of the disease management server output an alert to the provider associated with the user when a measurement value of the received biometric measurements is outside a range of normal measurement values.

6. The system according to claim 1, wherein the physical biometric measurement device transmits the biometric measurements, and the disease management server transmits the personalized notifications and the updated personalized notifications via one of a cellular channel or a wireless network.

7. The system according to claim 1, wherein each of the personalized notifications and the updated personalized notifications include one or more of recommendations for:
 (a) dosing and timing of medication;
 (b) combinations of two or more medications;
 (c) user dietary behavior;
 (d) timing of obtaining measurements by the physical biometric measurement device;
 (e) food intake;
 (f) time and amount of carbohydrate intake;
 (g) modification of user behaviors; and
 (h) educational materials for the user.

8. A method for providing personalized notifications using an adaptive analytical behavioral health assistant system, the method comprising:
 obtaining, using a physical biometric measurement device of the health assistant system, biometric measurements from a user;
 transmitting, from the physical biometric measurement device, the obtained biometric measurements;
 receiving, using a receiver of a disease management server of the health assistant system, the biometric measurements transmitted from the physical biometric measurement device;
 executing, using one or more processors of the disease management server, a basic model of a physiological system generic to any user to generate a modified model specific to a physiological system of the user, wherein generating the modified model comprises updating the basic model based on information specific to the physiological system of the user, wherein the modified model is configured to estimate an impact of a change in one or more factors on the physiological system of the user;
 executing, using the one or more processors, the modified model to generate personalized notifications, based on the modified model;
 learning, using the one or more processors, one or more effects of the received biometric measurements on the physiological system, and updating an ability of the modified model to estimate an impact of further changes in the one or more factors on the physiological system of the user, thereby creating an updated modified model by machine learning;
 executing, using the one or more processors, the updated modified model to generate updated personalized notifications; and
 outputting, from the disease management server to the physical biometric measurement device, and from the physical biometric measurement device to the user, the personalized notifications and the updated personalized notifications, based on modifying an internal signal of the physical biometric measurement device to output the personalized notifications and the updated personalized notifications to the user, such that the outputted personalized notifications and the updated personalized notifications are formatted and provided to the user over a network when they are received at the physical biometric measurement device.

9. The method according to claim 8, wherein a measurement is received by the receiver of the disease management server every time the physical biometric measurement device obtains a biometric measurement.

10. The method according to claim 8, wherein biometric measurements are received by the receiver of the disease management server at predetermined intervals.

11. The method according to claim 8, further comprising outputting, using the one or more processors, an alert to a provider associated with the user.

12. The method according to claim 11, wherein an alert is output to the provider associated with the user when a measurement value of the received measurements is outside a range of normal measurement values.

13. The method according to claim 8, wherein the physical biometric measurement device transmits the biometric measurements, and the disease management server transmits the personalized notifications and the updated personalized notifications via one of a cellular channel or a wireless network.

14. The method according to claim 8, wherein the physical biometric measurement device is selected from the group consisting of:
  (a) a glucose monitor, wherein the biometric measurements are glucose levels of the user;
  (b) a blood pressure measuring device, wherein the biometric measurements are blood pressure measurements of the user; and
  (c) a weight measuring device, wherein the biometric measurements are weight measurements of the user.

15. The method according to claim 8, wherein each of the personalized notifications and the updated personalized notifications include one or more of recommendations for:
  (a) dosing and timing of medication;
  (b) combinations of two or more medications;
  (c) user dietary behavior;
  (d) timing of obtaining measurements by the physical biometric measurement device;
  (e) food intake;
  (f) time and amount of carbohydrate intake;
  (g) modification of user behaviors; and
  (h) educational materials for the user.

16. A non-transitory computer-readable storage medium for storing instructions that, when executed by one or more processors, perform a method for providing personalized notifications using an adaptive analytical behavioral health assistant system, the method comprising:
  obtaining, using a physical biometric measurement device of the health assistant system, biometric measurements from a user, the physical biometric measurement device selected from one or more of a scale, an external blood pressure monitor, a cardiac data sensor, an implantable blood glucose sensor for continuous sensing, an external blood glucose monitor, a blood pressure measuring device for measuring blood pressure measurements of the user, or a weight measuring device for measuring weight measurements of the user;
  transmitting, from the physical biometric measurement device, the obtained biometric measurements;
  receiving, using a receiver of a disease management server of the health assistant system, the biometric measurements transmitted from the physical biometric measurement device;
  executing, using one or more processors of the disease management server, a basic model of a physiological system generic to any user to generate a modified model specific to a physiological system of the user, wherein generating the modified model comprises updating the basic model based on information specific to the physiological system of the user, wherein the modified model is configured to estimate an impact of a change in one or more factors on the physiological system of the user;
  executing, using the one or more processors, the modified model to generate personalized notifications, based on the modified model;
  learning, using the one or more processors, one or more effects of the received biometric measurements on the physiological system, and updating an ability of the modified model to estimate an impact of further changes in the one or more factors on the physiological system of the user, thereby creating an updated modified model by machine learning;
  executing, using the one or more processors, the updated modified model to generate updated personalized notifications; and
  outputting, from the disease management server to the physical biometric measurement device, and from the physical biometric measurement device to the user, the personalized notifications and the updated personalized notifications based on modifying an internal signal of the physical biometric device to output the personalized notifications and the updated personalized notifications to the user.

17. The computer-readable storage medium according to claim 16, wherein a measurement is received by the receiver of the disease management server every time the physical biometric measurement device obtains a measurement.

18. The computer-readable storage medium according to claim 16, wherein biometric measurements are received by the receiver of the disease management server at predetermined intervals.

19. The computer-readable storage medium according to claim 16, further comprising outputting, using the one or more processors, an alert to a provider associated with the user.

* * * * *